(12) United States Patent
Galibert et al.

(10) Patent No.: US 6,780,593 B1
(45) Date of Patent: Aug. 24, 2004

(54) METHOD FOR MAPPING A DNA MOLECULE COMPRISING AN AD INFINITUM AMPLIFICATION STEP

(75) Inventors: Francis Galibert, Saint-Gratien (FR); Yvon Cavaloc, Nouvelle Caledonie (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 0 days.

(21) Appl. No.: 09/958,211

(22) PCT Filed: Apr. 7, 2000

(86) PCT No.: PCT/FR00/00891

§ 371 (c)(1),
(2), (4) Date: Jan. 18, 2002

(87) PCT Pub. No.: WO00/61798

PCT Pub. Date: Oct. 19, 2000

(30) Foreign Application Priority Data

Apr. 8, 1999 (FR) .............................. 99 04388

(51) Int. Cl.[7] .............................. C12Q 1/68; C12P 19/34
(52) U.S. Cl. .......................................... 435/6; 435/91.2
(58) Field of Search ........................... 435/6, 91.2, 810

(56) References Cited

U.S. PATENT DOCUMENTS

| | | | | |
|---|---|---|---|---|
| 5,126,239 A | * | 6/1992 | Livak et al. .................... | 435/6 |
| 5,506,133 A | * | 4/1996 | Yu et al. .................... | 435/240.2 |
| 5,731,171 A | | 3/1998 | Bohlander ................. | 435/91.2 |

FOREIGN PATENT DOCUMENTS

| WO | WO97/10252 | 3/1997 |
|---|---|---|

OTHER PUBLICATIONS

P.H. Dear et al., "Happy Mapping: Linkage Mapping Using a Physical Analogue of Meiosis", Nucleic Acids Research, Vo. 21, No.1, pp. 13–20, 1993.

P.H. Dear et al., "A High–Resolution Metric Happy Map of Human Chromosome 14", Genomics, vol. 48, pp. 232–241, 1998.

D. Grothues, et al., PCR Amplification of Megabase DNA with Tagged Random Primers (T–PCR), Nucleic Acids Research, vol. 21, No. 5, pp. 1321–1322, 1993.

G. Walter, et al., "Happy Mapping of a Yac Reveals Alternative Haplotypes in the Human Immunoglobulin $V_H$Locus", Nucleic Acids Research, vol. 21, No. 19, pp. 4524–4529, 1993.

V.G. Cheung, et al., "Whole Genome Amplification Using a Degenerate Oligonucleotide Primer Allows Hundreds of Genotypes to be Performed on Less Than One Nanogram of Genomic DNA", Proc. Natl. Acad. Sci., U.S.A., vol. 93, pp. 14676–14679, 1996.

G. Gyapay et al., "A Radiation Hybrid Map of the Human Genome", Human Molecular Genetics, vol. 5, No. 3, pp. 339–346, 1996.

S. He et al., "Detection of DNA Sequence Polymorphisms Among Wheat Varieties", Theor Appl Genet, vol. 84, pp. 573–578, 1992.

P.H. Dear et al., "Happy Mapping: A Proposal for Linkage Mapping the Human Genome", Nucleic Acids Research, No. 17, pp. 6795–6807, 1989.

P.H. Dear, "Happy Mapping", Genome Mapping, IRL Press, Oxford, U.K., pp. 95–123, 1997.

* cited by examiner

*Primary Examiner*—Kenneth R. Horlick
(74) *Attorney, Agent, or Firm*—Finnegan, Henderson, Farabow, Garret & Dunner, L.L.P.

(57) ABSTRACT

The invention relates to a Happy Mapping type method for mapping a DNA molecule comprising a step enabling ad infinitum amplification of the DNA of each panel, consisting of the following: (i) a first amplification with the aid of a primer comprising 10–30 nucleotides defined at extremity 5' thereof, and 5–10 random nucleotides at extremity 3' thereof, in addition to (ii) a second amplification with the aid of a primer comprising at least the oligonucleotides defined at extremity 5' of the primer used in stage i.

20 Claims, 6 Drawing Sheets

FIG. 1A
DNA preparation

FIG. 1B
DNA fragmentation

Distribution per well

FIG. 1E

T-PCR amplification

1 DNA mother plate

Numerous daughter plates

FIG. 1F
Detection

Marker A  Marker B  Marker Z

FIG. 1G
Calculation of distances

METHOD FOR MAPPING A DNA MOLECULE COMPRISING AN AD INFINITUM AMPLIFICATION STEP

This application is based on and claims the benefit of French application 99/04388, filed Apr. 8,1999, and International application PCT/FR00/00891, filed Apr. 7, 2000. The entire disclosure of these applications are relied upon and incorporated by reference herein.

The present invention relates to a method for mapping a DNA molecule of the Happy Mapping type which comprises a step for ad infinitum amplification of the DNA of each panel. The present invention also relates to a kit for implementing this mapping method and to the use of the maps obtained for identifying genes imparting a phenotype of interest.

The emergence of a great number of genome sequencing projects and notably that of the human genome inevitably requires the development of novel fast and accurate mapping methods in order to carry out the assembling of raw data from systematic sequencing. Moreover, if the present trend of proceeding with shotguns of entire genomes is confirmed, detailed genomic maps will need to become available.

More than a dozen of microbial genomes have already been fully sequenced, as a result of a direct shotgun sequencing of their genome tigr.org/tdb/mdb.mdb.html). However, the latter have sizes from 580 kb to 4 Mb. The use of such an approach for sequencing larger genomes such as the human genome (3 000 Mb), as suggested by Weber and Myers, 1997, and announced by Venter et al., 1998 does however give rise to certain questions. Indeed, the large size of these genomes and the presence of many repeated sequences makes the assembling of the sequencing results difficult. Thus, it proves necessary to have detailed genomic maps in order to allow these data to be processed.

The drawing up of detailed genomic maps may also be very helpful for phylogenic studies. Indeed, studies on the evolution of genomes have clearly shown that the expression of many genes depends on their localization in a certain genetic context. Recent developments in genomics now allow the evolution of genomes to be studied in more detail on the basis of syntenic relationship changes. With detailed maps, obtained for two species, genetic links which have been maintained between these two species during evolution, may be assessed.

Another field for which the provision of detailed genetic maps would be of fundamental interest, is the localization of QTL (Quantitative Trait Loci). Indeed, most variations within a population or among different races, for example, are of a quantitative nature. Certain variations such as the size, the weight of individuals, the flowering date for plants or the amount of milk produced in mammals are not included in well-defined classes according to Mendelian proportions, but rather they operate in a continuous manner, according to a gradient from one extreme to the other. These variations preserved in the line of descent, are therefore transmitted genetically. The loci involved in the variation of quantitative phenotype traits are called QTL. Detection of links between a QTL and genetic markers provide a robust method for identifying these QTL. It is possible to localize a QTL by the so-called "interval mapping" (Lander et Botstein, 1989) method between two informative markers separated by more than 20 cM. However, such an interval makes the identification of the gene, problematical. Also, it is quite useful to be able to perform a zoom on the region of interest if a large number of markers are available, and to perform a fine mapping, in order to localize the sought-after gene specifically.

A conceivable mapping approach is the mapping by radiation hybrids (RH, Radiation Hybrid mapping) (Cox et al., 1990; Gyapay et al., 1996). It consists in irradiating cell lines, causing chromosomal random breaks. The different fragments of generated chromosomes are then integrated into the genome of the rodent cells. Thus, it is possible to determine the distance separating two markers by knowing that the closer they are, the more likely they will be incorporated within a same fragment and therefore be detected in a same line. However, this approach has certain drawbacks in addition to its cumbersomeness in the setting-up of a panel of radiation hybrids. Indeed, (i) certain loci which would not be cloned, cannot be integrated into a genome map; (ii) the interpretation of results may be confusing when the inserts are rearranged or ligated with each other; (iii) the presence of exogenous DNA, in this case the one of the hamster host cell, very often requires that a certain number of markers be set aside, those giving a positive response with this exogenous DNA.

With the more flexible Happy Mapping method, the different problems (Dear and Cook, 1993) may be circumvented. With this method, both events analyzed by cross-breedings of formal genetics, i.e. crossing-over and segregation, may be reproduced in vitro. In practice, crossing-over is mimicked by a random break of DNA into fragments, the size of which depends on the sought-after mapping. The markers are then segregated by a random distribution of these fragments into deposits of at least one equivalent of haploid genome per aliquot, then detected by PCR. Those which are genetically linked, tend to remain together in the same aliquot whereas those which are not linked, are randomly distributed. Their order and the distance which separate them may be inferred from the sequence of their co-segregation by a statistical calculation. It is important to remind here, that a panel which may be used for Happy mapping, is simple to produce as it only requires a few days or even a few weeks. In addition, it may be adapted to any resolution level, according to the size of the selected fragments and may even result in molecular cloning of fragments of interest for sequencing.

The Happy Mapping method comprises the following steps:
a) Genomic DNA is broken by irradiation,
b) About one equivalent of haploid genome is then placed in each well of a 96-well plate, which corresponds to about 60% of the initial genomic DNA (statistical distribution of the markers).
c) the DNA is amplified by PCR,
d) and the markers are then detected.

This mapping method has already proved to be reliable for genomes as different in size as the human chromosome 14–100 Mb—(Dear et al., 1998) or that of a parasite protozoan of the intestinal epithelium of many mammals, Cryptosporidium parvum—10 Mb—(Piper et al., 1998). However, for these two investigations, no satisfactory method was described for amplifying the initial panel, for mapping an unlimited number of markers and any kind of markers. In Dear et al., only a small portion of the total DNA, flanked by repeated sequences was able to be mapped. In Piper et al., the amplification level was not sufficient for providing direct detection of the markers by PCR. These authors had to proceed with nested PCR in order to view the markers to be mapped. Further, the amplification method used only allows a limited number of markers to be mapped, requiring a mapping panel to be reconstructed in order to localize further markers.

In order that the amplification method may be contemplated for Happy mapping, it should meet the following three criteria:

(i) A DNA amount close to one equivalent of haploid genome should be sufficient as a matrix;
(ii) the entire genetic information should be amplified;
(iii) the formed panel should be able to be re-amplified ad infinitum in order to provide mapping of an illimited number of markers.

Thus, the problem consists of amplifying the entire DNA in each well, whereby said amplification should not produce artefacts in the random distribution of markers. The objective is the development of an approach for total homogeneous and ad infinitum amplification of genomic DNA.

The conventional PCR technique has evolved, providing many amplification methods each having their own specificity. For example, it is possible to amplify several sequences simultaneously by using several pairs of primers in a same reaction tube, Apostolakos et al., (1993). However, the number of primer pairs rarely exceeds 3. Indeed, above, the amplifications lose their specificity. Other techniques, more or less derived from PCR, have been developed: LCR, Gap-LCR, ERA, CPR, SDA, TAS, NASBA. However, none of these amplification techniques seems to provide an adequate solution for total amplification of DNA.

The T-PCR technique consists of a first amplification step by means of primers containing on their 3' end, random sequences reproducing all possible combinations, and a defined sequence on their 5' end. Under these operating conditions, these oligonucleotides will randomly pair up over the whole length of the sequence and the amplification cycles will provide incorporation of said defined sequences into all the amplified fragments. The second step consists of amplifying the fragments obtained in the first step by means of a primer including the defined sequence of the 5' end of the primers of the first step, exclusively. This technique has been described in U.S. Pat. No. 5,731,117 and Grothues et al., 1993. According to the authors, this method provides amplification of DNA fragments of 400 pb and also of genome fragments which may have up to 40 megabases. For a PCR technique to be applicable to Happy Mapping, the amplification should be general, while not introducing any selection (bias) in the portions of amplified DNA. Now, this point has only been tested by hybridization, which is not demonstrative. Moreover, U.S. Pat. No. 5,531,117 shows that total amplification may only be performed if at least 17 DNA equivalents are available initially. A priori, this shows that the T-PCR amplification method cannot be used for mapping with the Happing Mapping method, as basically, DNA amounts which only correspond to 1 equivalent should be amplified. Further, the amplification step is discussed in U.S. Pat. No. 5,731,117 in order to obtain markers and not for preparing the substrate on which the markers will be positioned. The fact that the inventor of the actual Happy Mapping did not retain T-PCR, but rather NESTED-PCR during subsequent development of his technique, proves that the technique as described and tested by hybridization did not seem to be satisfactory. The solution found within the framework of the present invention was to adapt T-PCR to Happy Mapping. The developed methodology is found to be advantageous for amplifying the entire DNA in each well without introducing any artefacts. Consequently, this amplification method represents a technical aid so that Happy Mapping may be implemented to its full extent.

Thus, the present invention relates to a method for mapping a DNA molecule, characterized in that it comprises the steps:

a) Breaking the DNA molecule in order to obtain DNA fragments, the size of which depends on the selected resolution, b) distributing said fragments in receptacles in order to have a DNA amount between about 0.5 to 1.5 DNA haploid genome equivalents per receptacle,
c) amplifying the DNA contained in the receptacles by an amplification method comprising the following steps: i) A first amplification by means of a primer comprising 10 to 30 defined nucleotides on its 5' end, and 5 to 10 random nucleotides on its 3' end, and ii) a second amplification by means of a primer comprising at least the defined oligonucleotide of the 5' end of the primer used in step i),
d) detecting the presence or absence of markers in the receptacles.

Preferably, the primer used in step i) includes 20 defined nucleotides at its 5' end, and 6 random nucleotides at its 3' end. In this case, the primer used in step ii) may include the 20 defined nucleotides at the 5' end of the primer used in step i).

Quite advantageously, the primer used in step i) corresponds to sequence SEQ ID NO.1 and the primer used in step ii) corresponds to sequence SEQ ID NO.2.

This amplification method therefore lies in two complementary steps. The first phase consists of an amplification with only one oligonucleotide as described above and the reaction is carried out in a final volume of 30 to 70 µl per microplate well, preferably 50 µl, with 3 to 7 units, preferably 5 units of AmpliTaq polymerase (Perkin Elmer). Any polymerase equivalent to AmpliTaq may be used with 2 to 6 µM of primer, preferably 4 µM.

The PCR reaction may be performed in the following way (@ means "at" or "at about"): 1×[5 mins at 95° C.; 50×(45 secs @92° C. 2 mins @37° C., 37° C.–55° C. 0.1° C./sec. 4 mins @55° C.]: 15×[45 secs @92° C., 1 min @55° C., 3 mins @72° C.]; 1×[5 mins @72° C.]. Of course, any equivalent cycle may be implemented in order to perform the invention.

For the second phase of the reaction, 1/20th to 1/200th, preferably 1/50th of the obtained product during the first phase is used as a matrix. The PCR reaction may be carried out in a final reaction volume from 5 to 20 µl, preferably 10 µl per microplate-well. Taq DNA polymerase (Promega) may be used with 0,5 to 3 µM, preferably 1.5 µM of primer as defined above (primer for step ii)). The PCR reaction may be carried out according to the following cycle 1×[2 mins @94° C.]: 50×[30 secs @92° C., 45 secs @54° C., 3 mins @72° C.]; 1×[5 mins @72° C.].

Of course, the parameters of this amplification method may be changed or adapted by one skilled in the art, according to the individual case.

Within the scope of the invention, a "DNA molecule", means a molecule which corresponds to a genome, a chromosome, or to a fragment of a genome or a chromosome. In addition, said molecule may be issued from a genome or a chromosome which has possibly undergone changes and/or processing.

A preferred embodiment of the invention, consists of extracting the DNA molecule from cells encapsulated in agarose blocks, then lyzed in order to release said intact molecule. Said cells may correspond to any cell from the plant, animal, or bacterial kingdoms.

The isolated DNA molecule is then broken by γ irradiation, by enzymatic digestion, notably by the action of endonucleases, such as for example restriction enzymes, or by a mechanical action. The obtained DNA fragments may be separated by means of any separation technique known to one skilled in the art, notably by electrophoresis, preferably by electrophoresis with pulsed fields for obtaining large size fragments before distribution (step b) in the method described above.

The microtitration plates are advantageously used as a receptacle. The fragments are thereby distributed into the 96 wells of a microtitration plate. For this purpose, the fragments are distributed in order to have an amount of DNA per receptacle (preferably per well) of about 1 equivalent of haploid genome, i.e. of the order of 2 pg for a mammal genome, for example.

Thus, the mapping method according to the invention is also characterized in that it comprises a step for amplifying the entire genetic information contained in the receptacles.

The DNA, amplified in each well, may then be distributed in order to prepare daughter plates. In this case, the markers are detected in the wells of the daughter plates. However, detection of the markers may also be directly carried out in the wells of the mother plate but in this case only a limited number of markers may be analyzed.

The markers, likely to be present in the wells, may be amplified by means of specific primers before the detection step. Detection is usually carried out after electrophoretic migration in a gel appropriate to the fragment size. The detection may also be carried out by means of probes specific to the markers. These probes may be capture probes, directly or indirectly fixed on a solid support or probes in the free state. A "capture probe" is or may be immobilized on a solid support by any appropriate means, for example by covalence, by adsorption or by direct synthesis on a solid support. These techniques are notably described in Patent Application WO 9210092, incorporated by reference herein. A "detection probe" may be marked by means of a marker for example, selected from radioactive isotopes, enzymes, in particular enzymes able to act on a chromogenic, fluorigenic or luminescent substrate (notably a peroxidase or an alkaline phosphatase), chromophore chemical compounds, chromogenic, fluorigenic or luminescent compounds, analogues of nucleotidic bases, and ligands such as biotin. The detection methods in 96-well microplates are within the capability of one skilled in the art.

For example, the PCR amplification product is denaturated and hybridized in a microplate well on which is fixed a capture oligonucleotide, Running (1990), or a single strand DNA containing a capture sequence, Kawai (1993). At least one of the primers used in PCR, for example is biotinylated and detection of hybridization is performed by adding streptavidin coupled with an enzyme such as peroxidase, then a chromogenic substrate for the enzyme. By using a capture oligonucleotide fixed on the wells, a biotynilated PCR primer and an internal standard for amplification, even quantitative PCR was made feasible, Berndt (1995). These publications are incorporated by reference herein.

A preferred embodiment of the present invention lies in the detection of markers on DNA chips. The principle of this technique consists in identifying DNA sequences on the basis of a molecular hybridization. The chip bears, grafted on an adequate surface, hundreds or thousands of oligonucleotides of interest or PCR products corresponding to markers for which a map is desired. The DNA of the wells is denaturated, marked and then placed under the hybridization conditions with the chip. The advantage of chips lies in their capability of providing hundreds, or even thousands of pieces of information from a single DNA sample. Further, the general experimental diagram is very simple and fast.

Another aspect of the invention relates to a kit for mapping a DNA molecule characterized in that it provides implementation of the method according to the invention. This kit may notably comprise a primer comprising 10 to 30 defined nucleotides at its 5' end and 5 to 10 random nucleotides at its 3' end, and/or a primer comprising at least the defined oligonucleotides of the 5' end of the aforementioned primer. Preferably, the kit comprises a primer of sequence SEQ ID NO.1 and/or a primer of sequence SEQ ID NO.2. The kit mentioned above, is therefore useful for preparing panels necessary for drawing up genomic or chromosomal maps.

Another aspect of the invention concerns DNA molecule maps obtained by the method according to the invention, or by any other equivalent method, and the use of said maps for identifying genes imparting a phenotype of interest (notably in plants), for identifying genes responsible for hereditary diseases, notably in humans, for identifying quantitative trait loci (QTL). Another aspect concerns the use of maps according to the invention as an aid for reconstructing massive shotguns for sequencing a DNA molecule.

Reference will be made to the captions of the figures shown hereafter in the continuation of the description.

BRIEF DESCRIPTION OF THE DRAWINGS

FIG. 1: Illustration of the method according to the invention. Three randomly selected markers on the genome are illustrated (A, B and Z). The different Happy mapping steps are detailed in FIG. 1, as follows:

(FIG. 1A) Genomic DNA is prepared from cells encapsulated in agarose, (FIG. 1B) it is randomly fractionated, (FIG. 1C) and the fragments are selected at a given size by pulse-field electrophoresis, (FIG. 1D) next, deposited in a microtitration plate in an amount of 1 equivalent of haploid genome per well.

(FIG. 1G) The co-segregation frequency of the markers enables their respective position to be determined and a physical map to be drawn up. Calculation of the marker association frequency (LOD score): the association frequency of the markers in a same well depends on the distance which separates them. Two close markers are often or always present together (case of markers A and B) and two remote markers are randomly associated (case of markers A and Z or B and Z).

FIGS. 2A and 2B: Results of the mapping according to the invention The region of the human chromosome 2 is indicated on the left of FIG. 2A and continued in FIG. 2B. The map was generated by associating the markers two by two with a LOD score larger than 4. The markers indicated on the right portion of the map were unambiguously positioned with respect to each other. The "floating" markers located on the left portion of the map exhibit strong association (LOD score larger than 6) with the markers facing them, but only exhibit low association with adjacent markers. The localization of the centromere is indicated by a dotted line.

FIGS. 3A and 3B: Comparison of the mapping results Three maps are illustrated in FIGS. 3A and 3B. The genetic map (left) includes the polymorphic markers localized by family studies. The map created by radiation hybrids (middle) results from the localization of both polymorphic and non-polymorphic markers on the G3 panel (Deloukas et al., 1998). The right map was obtained with the method according to the invention. The markers positioned on two different maps are illustrated by fine lines joining both maps. The localization of the centromere is indicated by a dotted line.

The present invention therefore provides a novel method for tackling ad infinitum amplification of a small amount of genomic DNA, about 1 haploid genome equivalent, i.e. about 2 pg in the case of the human genome—required for forming a panel which may be used for mapping. The developed technique achieved in two PCR steps provides amplification of almost the entire genetic contents. This approach enables a large number of markers to be mapped on a portion of the human chromosome 2. The results of the mappings carried out by implementing the method according to the invention are in agreement with all the data described in the literature. The method according to the invention is simple to reproduce as it only requires a few days or even a few weeks. In addition, it is suitable for any resolution level, according to the size of the generated and selected fragments. It may even result in the molecular cloning of fragments of interest for sequencing.

The most critical step in the described technique is the step for total and homogeneous amplification of the genome. The solution suggested by Paul Dear, inventor of the Happy Mapping method is the use of primers anchored on repeated elements all along the genome (Alu, LINE) (IRS-PCR, i.e. Interspersed Repetitive Sequence-PCR). This solution has enabled a thousand markers to be positioned on the human chromosome 14 (Dear et al., 1998). However, IRS-PCR is limited to amplification and therefore to the mapping of markers close to the repeated sequences and flanked by them. This type of amplification is therefore restricted to a small portion of the genome (as only the sequences flanked by two Alu or LINE sequences are amplified) and is only applied to the human genome or the genome of primates, unless specific amplification conditions are defined for each investigated organism. This is why the object of the present invention consists in a technique for uniformly amplifying the genome whatever the genome, without losing any markers. In order to be able to use it for mapping of the Happy Mapping type, the amplification method should be both quantitative (it should amplify at a sufficient level a small quantity of initial DNA corresponding to about one genome equivalent) and qualitative (no notable loss of genetic information).

As mentioned earlier, various approaches has been considered for solving the problem. The first three from the literature (Telenius et al., 1992: Zhang et al. 1992; Grothues et al., 1993), have only afforded few results. The method by Telenius et al. (1992) uses a degenerated oligonucleotide on 6 positions for a PCR amplification achieved in only one step (DOP-PCR, i.e. degenerated oligonucleotide primed-PCR). But this method only works if a large amount of initial material is available (100 nm of human genomic DNA, i.e. about 50,000 haploid genome equivalents, or 50,000 copies of an isolated chromosome). Now a mapping of the Happy Mapping type is only possible from DNA samples for which the amount is close to one haploid genome equivalent. By using the conditions described by Telenius et al., it is not possible to obtain amplification of more than 50% of the initial genetic material. This is in agreement with the results of Cheung and Nelson (1996) which show that the smaller the amount of genomic DNA used as a matrix, below a threshold of 600 pg—i.e. 300 haploid genome equivalents in the case of a mammal genome,—the higher is the risk of not amplifying a locus.

The second method described by Zhang et al. (1992) uses an entirely degenerated oligonucleotide on its 15 positions (PEP, Primer Extension Preamplification). By varying the PCR conditions used by Zhang et al. (number of cycles, hybridization temperature, primer concentration), it seemed possible to amplify nearly 90% of the DNA matrix into a minimum of 200 copies. However, this approach does not provide further preamplification and therefore greatly limits the number of markers which may be mapped. Further, the amplification level does not enable the amplification product of a given marker to be directly viewed but forces the use of two pairs of primers, the second being nested in the first, and therefore an amplification is carried out in two steps.

Another approach is carried out in two steps and is based on a degenerated oligonucleotide on the 9 residues located in its portion 3' and including a fixed sequence at 5' used for the second amplification step (T-PCR, Tagged-PCR) (Grothues et al., 1993). However, there is no emphasis here on a qualitative aspect of the amplification. It has therefore been necessary to determine whether the quantitative and crucial qualitative parameter would be compatible with Happy mapping. In addition, it is clearly shown in U.S. Pat. No. 5,731,171 that the lower limit for amplification is 17 genome equivalents, which cannot be contemplated in Happy Mapping. Another significant drawback in the method described in U.S. Pat. No. 5,731,171 is the risk of contamination by foreign DNA. Indeed, during the low stringency amplification step, each cycle requires "manual" introduction of DNA polymerase. As the number of cycles has to be increased for very small amounts of DNA, the risk of contamination is all the more increased.

All these difficulties have been set aside by the present invention. The performed investigations actually have enabled a PCR type method to be used within the framework of Happy Mapping. The first amplification step should advantageously comply with parameters such as the primer concentration, the number of PCR cycles, the hybridization temperature, as well as the length of the degenerated chain at 3'. The selection of the fixed sequence at 5' of the oligonucleotide is important for the second amplification step. This second phase is itself also very dependent on the amount of used primer and of the number of achieved PCR cycles.

Mapping Method Comprising an ad Infinitum Amplification Step.

Figure 1:
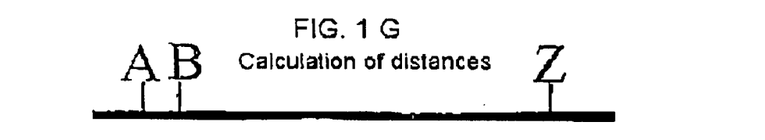
Figure 1A:
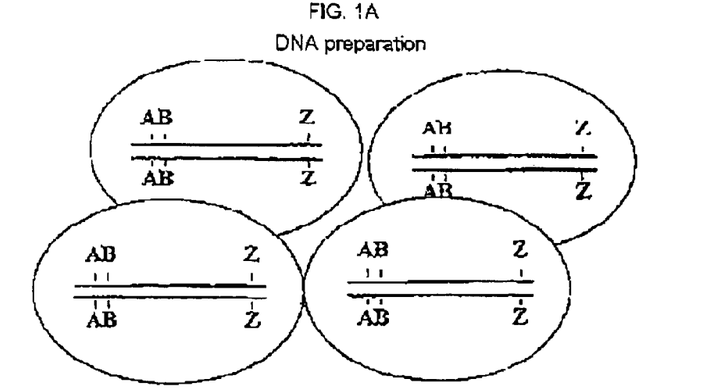
Figure 1B:
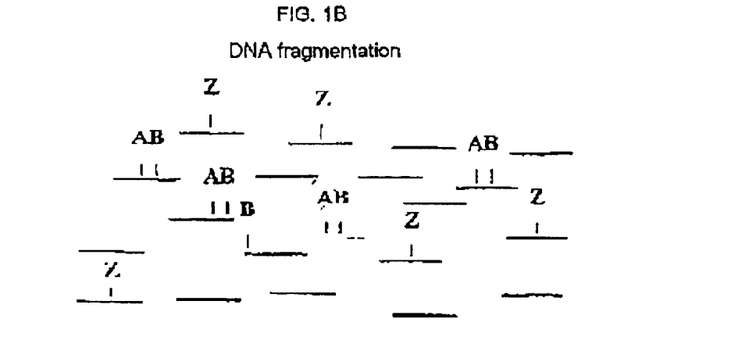
Figure 1C:
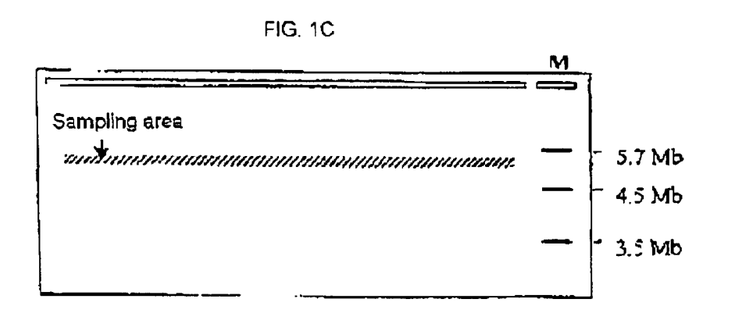
Figure 1D:
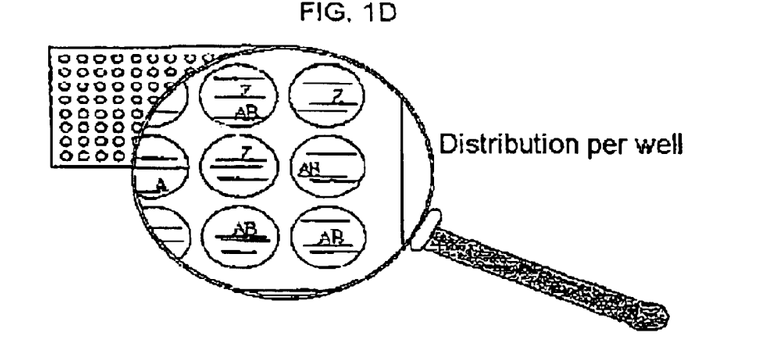

Cells collected from the subject under investigation are encapsulated in agarose blocks (FIG. 1A), and then lyzed in order to release intact DNA. According to the size of the desired fragments, DNA is then broken up, or involuntarily broken up at random (by γ irradiation, enzymatic digestion or mechanical action) in order to obtain fragments for which the size depends on the selected resolution (FIG. 1B). DNA is then caused to migrate by pulsed field gel electrophoresis (PFGE) in order to separate fragments with homogeneous sizes (FIG. 1C), which are distributed in the 96 wells of a microtitration plate in order to only have an amount close to one DNA haploid genome equivalent per well (FIG. 1D). In this way, each well has an incomplete representation of the genome which is specific to it. The entire genetic information contained in each well is then amplified by PCR.

Figure 1E:
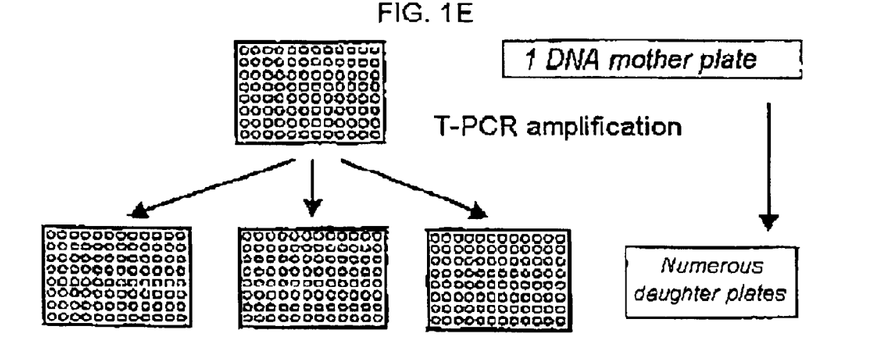
(FIG. 1E) This will form the mapping panel after amplification by two PCR steps.
Figure 1F:
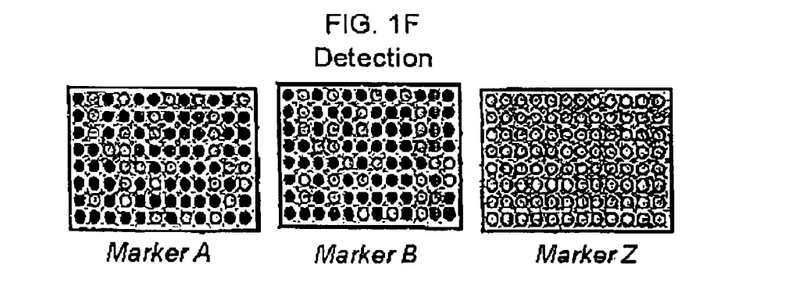
(FIG. 1F) Each daughter plate is then used for mapping a marker. PCR is carried out with specific primers and here the analysis is performed on an agarose gel.

Each well now contains a large amount of DNA so that this material may be distributed in a great number of daughter plates (FIG. 1E). Hence, each daughter plate will be used for determining the distribution of a marker or of a limited number of markers if detection is achieved through electrophoresis, for example by means of PCR by using specific oligonucleotides of the relevant marker (FIG. 1F) as primers. The PCR products are then analyzed with conventional electrophoresis on an agarose gel. This operation is repeated for a large number of markers.

If one equivalent of genome is distributed per well, each marker will be found again in 65% of the wells (Poisson's law). Two non-linked markers (separated by a distance larger than the mean size of the aliquot fragments) will be randomly distributed and found together in 42% of the wells (65%×65%). Conversely, two markers separated by a distance less than this average size would segregate all the more frequently together that they are close to one another, up to the point of being found together in 65% of the aliquots in the case of very closely linked markers. Each occurrence is recorded and the links between the markers are calculated (lod score), like in conventional genetics, by means of computer software packages such as RHmap (Boehnke et al., 1991) or RHmapper (Slonim et al., 1995). The frequency of association between two markers, expressing the physical distance which separates them on the chromosome, then enables a map to be inferred, which groups together all the associated markers, two by two, within a same link group (FIG. 1G).

EXAMPLE 1

Mapping of Markers on the Human Chromosome 2

Materials and Methods a) Preparation of the Mapping Panel

Human lymphocytes are sampled and purified on Ficoll (Ficoll pack—Pharmacia) according to instructions provided by the supplier. After counting, the cells are encapsulated in agarose blocks (InCert—FMC) in an amount of $10^5$–$10^6$ cells/ml of agarose, and then lyzed in situ by 5 successive washes, spread out over 48 hours, in 500 ml of a lysis solution (10 mM Tris-HCl pH 7.4; 1 mM EDTA; 1% LiDS) in order to release the intact DNA. The agarose blocks are then equilibrated in the same LiDS-free solution. During these steps, the DNA is randomly fractionated so that the average size of the resulting fragments is close to 6–7 Mb (results not shown). The DNA is then caused to migrate by electrophoresis with pulsed fields (Pulsed Field Gel Electrophoresis) (PFGE) in a CHEF Mapper (BioRad) [on agarose gel 0,8% (SeaKem Gold agarose—FMC) in TAE IX: migration at 2V/cm in TAE IX for 96 hours @14° C.: field inversion period of 40 mins 23 secs at 106°][3]. After 48 hours of migration, the wells as well as the upper 2 mm of gel are removed in order to avoid any contamination by small DNA fragments which would be trapped in the wells and gradually salted out during electrophoresis. Upon completion of the migration, the portion of the gel containing the size markers (chromosomes of S. pombe—FMC) is colored with BET. The genomic DNA is then sampled from the gel by means of glass microcapillaries (Minicaps 10 μm—Hirschmann Laborgerate) and then these agarose samples are distributed in the 96 wells of a microtitration plate in order to have only 2 pg of DNA per well i.e., a little less than one equivalent of haploid genome [4]. In this way, each well has an incomplete representation of the genome which is specific to it.

The first step consists of determining the amount of DNA present in the wells and adjusting it as required, to about 2 pg for human material. For this analysis, a marker is randomly selected on each human chromosome in order to determine the amount of DNA to be distributed in the mother plate. If one starts with one haploid genome equivalent, each marker should be present in 65% of the analyzed wells, according to Poisson's statistical law (Dear et al., 1993), which is checked by nested PCR.

b) Random Amplification of Genomic DNA

The DNA content of each well is amplified in two steps by PCR. The first step consists in an amplification using only one oligonucleotide (T3N6 5' AATTAACCCTCAC-TAAAGGGNNNNNN 3') (SEQ ID NO.1) The reaction is performed in a final volume of 50 μl, per well of the microplate, containing 50 mM KCl: 10 mM Tris-HCl pH 8.3; 0.001% (w/v) gelatin; 2.5mM $MgCl_2$; 200 μM dNTP (Pharmacia); 5 units of AmpliTaq polymerase (Perkin Elmer) and 4 μM of T3N6 oligonucleotide. Each test is covered with a drop of mineral oil and the PCR reaction is carried out in a thermocycler PTC-200 (MJ Research) 1×[5 mins @95° C.]; 50×[45 secs @92° C., 2 mins @37° C., 37° C. 0.1° C./sec, 4 mins @55° C.]: 15×[45 secs @92° C., 1 min@55° C., 3 mins, 3 mins @72° C.]; 1×[5 mins @72° C.].

For the second phase of the reaction, ⅕₀th of the first phase is used as a matrix. The PCR reaction is carried out in a final reaction volume of 10 μl, per well of the microplate, containing 50 mM KCl; 10 mM Tris-HCl pH 9; 0.1% Triton® X-100; 2.5 mM $MgCl_2$; 300 μM dNTP (Pharmacia); 2 units of Taq DNA polymerase (Promega) and 1.5 μM of T3 oligonucleotide (5' AATTAACCCTCACTAAAGGG 3') (SEQ ID NO.2). The PCR reaction is carried out in a thermocycler PTC-200 (MJ Research): 1×[2 mins @94° C.]: 50×[30 secs @92° C., 45 secs @54° C., 3 mins @72° C.]; 1×[5 mins @72° C]. This second phase is carried out four times, independently, and then the four reactions are mixed together.

c) Creation of a Map of a Portion of the Human Chromosome 2

Materials and Methods

Analysis of the marker distribution

EST (Expressed Sequence Tag) type markers as well as a few markers of the microsatellite type already mapped were selected in the following databases on the human chromosome 2: ncbi.nlm.nih.gov/genemap ncbi.nlm.nih.gov. SCIENCE96/shgc.stanford.edu/Mapping/rh/MapsV2/search2.html The marker distribution in each daughter plate is analyzed by PCR from 1 microliter of the second amplification phase. The reaction medium contains 50mM KCl; 10 mM Tris-HCl, pH 9.0; 0.1% Triton X-100; 2.5 mM $MgCl_2$; 250 μM of each dNTP; 1 μM of both specific upstream and downstream oligonucleotides of each analyzed marker and 0.5U of Taq DNA polymerase (Promega) in 10 μl. The reaction comprises a first denaturation cycle of 1 min at 92° C., followed by 20 cycles of 20 secs at 92° C., 30 secs at 60° C. with a temperature decrement of 0.5° C./cycle and 30 secs at 72° C. and then 10 cycles of 20 secs at 92° C., 30 secs at 50° C., and 30 secs at 72° C. as well as 1 elongation completion cycle of 2 mins at 72° C.

After migration on 3% agarose gel, the PCR products are viewed and photographed on a UV plate equipped with a CCD camera (Bioprint).

Computer Processing

Subsequently, the presence/absence of each marker in the wells of the microplates is manually entered on the computer as a trinary number including the digits 0 (marker absent), 1 (marker present) or 2 (doubtful result), interpretable by conventional mapping software packages. The various link groups are then formed, after association frequency calculations for the markers (LOD score), by means of the RH2PT program from the set of RHMAP software packages (Boehnke et al., 1991). The distances separating the markers as well as their order are finally determined by means of the RHMAXLIK program of this same set.

Results

Figure 2A:
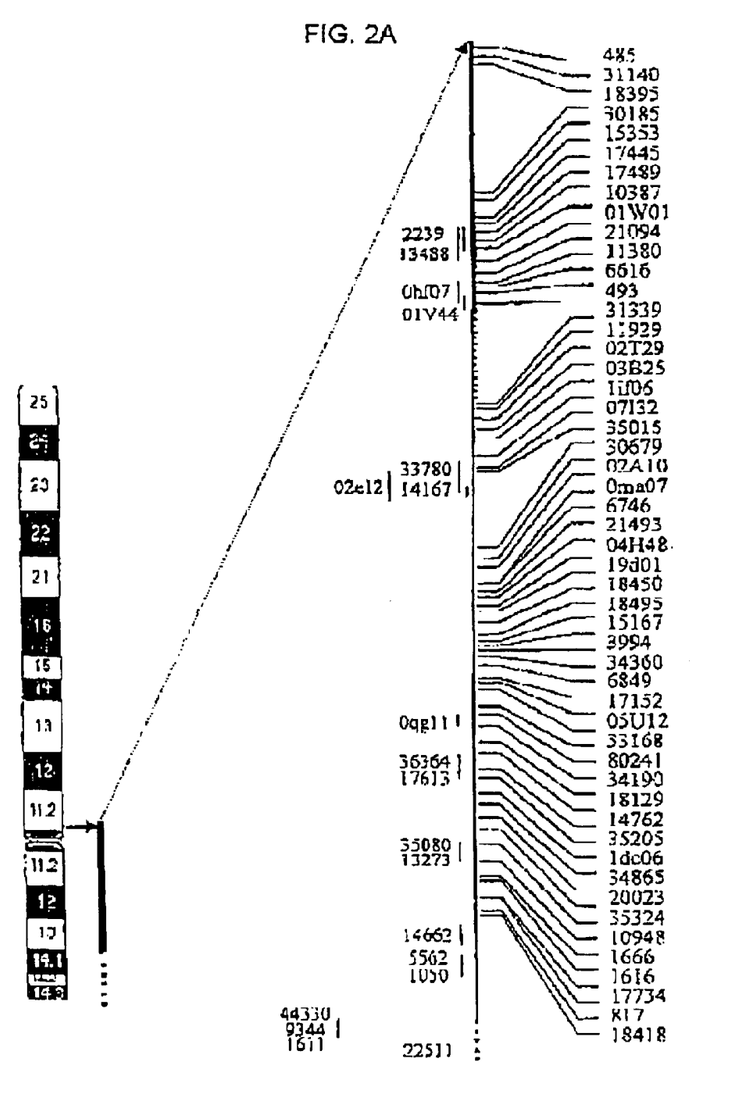
Figure 2B:
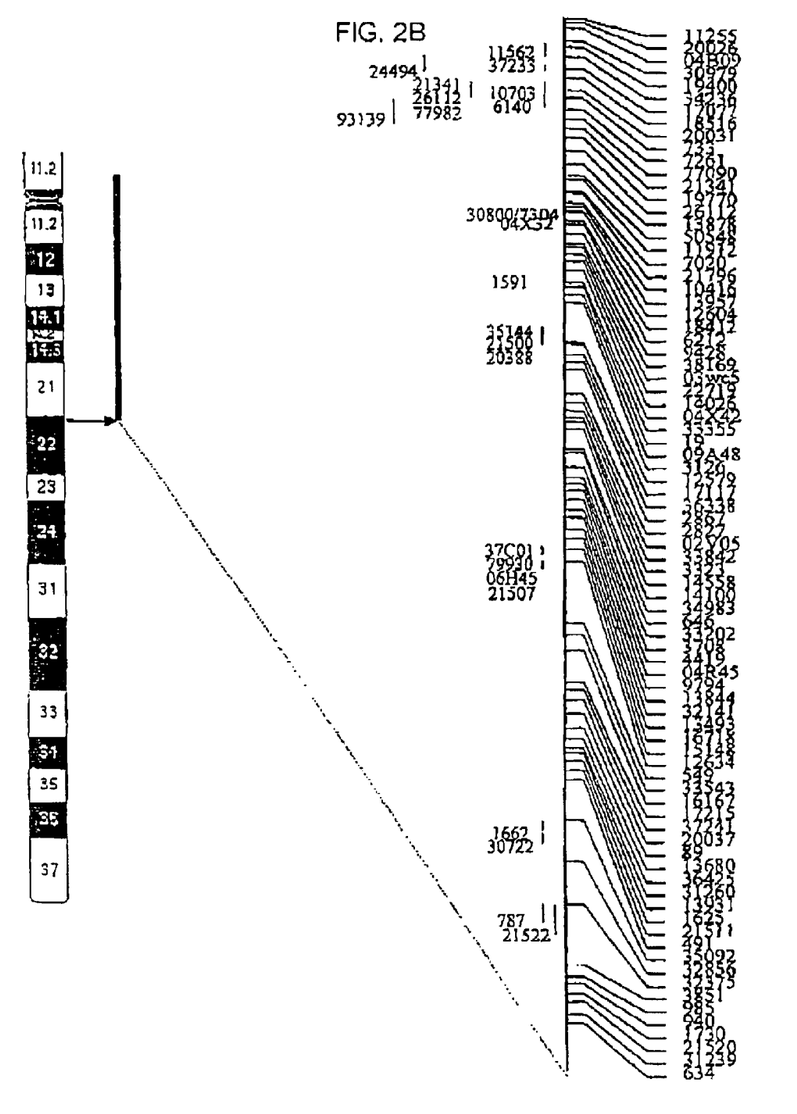

In a first phase, 190 human markers were selected in the databases on an area covering about 60 megabases of the human chromosome 2. Each of these markers was tested by PCR on the wells of the microplate forming the mapping panel. The presence/absence of these markers is viewed by PCR followed by electrophoresis and coloration with BET. Among these 190 markers, 176 a were integrated into the map (>92%; FIG. 2). The other ones were discarded because of a retention rate much too far away from the norm. Indeed, only markers for which the number of positives is $p\pm 2\sqrt{(p-[p^2/n])}$ wherein p is the average number of positives per marker and n is the number of aliquots forming the panel, are retained. Statistical analysis of the marker distribution is carried out by means of the software series RHMap (Boehnke et al., 1991). In a first phase, a first grouping of markers is performed by a 'two by two' analysis by fixing a minimum LOD score threshold of 8 for viewing the association between the markers. The markers were placed with respect to their neighbors by a multipoint analysis within each link group generated at a LOD score of 8. Subsequently, the groups were positioned relatively to each other by choosing a LOD score of 4.

Among the 176 markers marked in this way, 133 were placed unambiguously relative to each other (>175%, FIG. 2). However, 43 other markers (left portion of the map; FIG. 2), showing a sufficiently strong association with one or several markers already localized for their being accepted as real, could not be placed formally because of a lesser association with markers located in close vicinity. For this reason, they have been marked with floating bars. It should be noted that if the map was obtained with 176 markers (density of 1 marker/340 kb), similar results would have been obtained by only using 75 carefully selected markers which would bring the minimum density down to 1 marker/800 kb).

EXAMPLE 2

Comparison of the HAPPY Map with the Other Maps Available in Databases

Figure 3A:
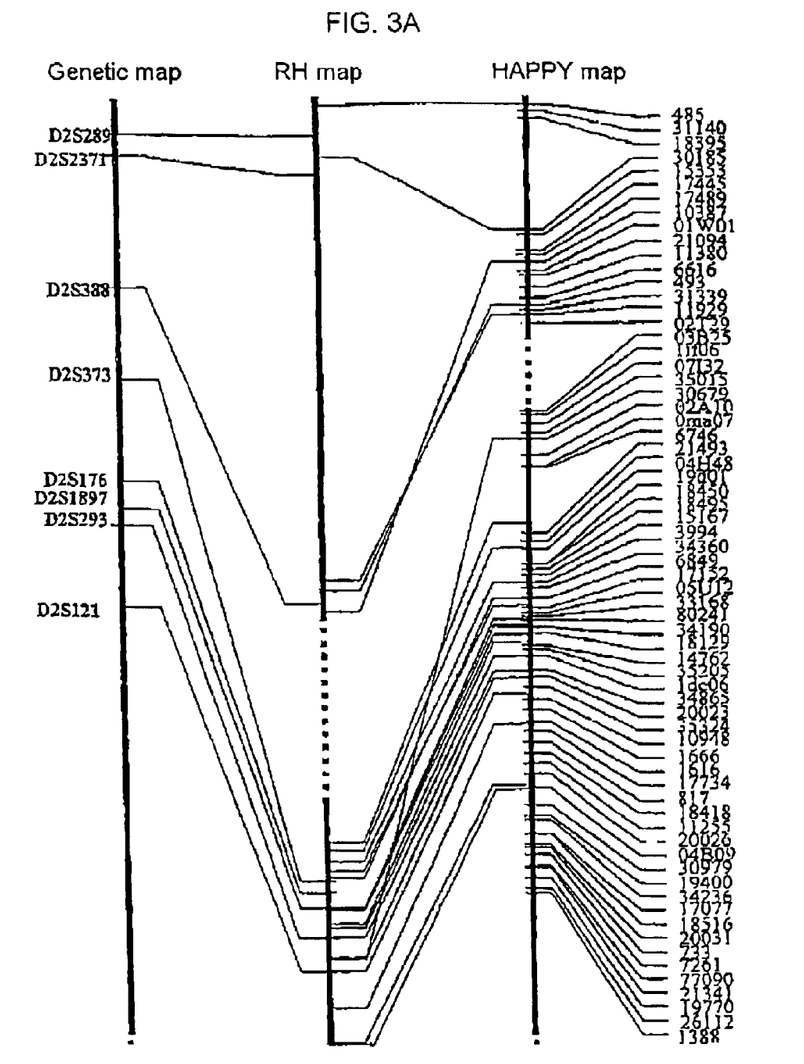
Figure 3B:
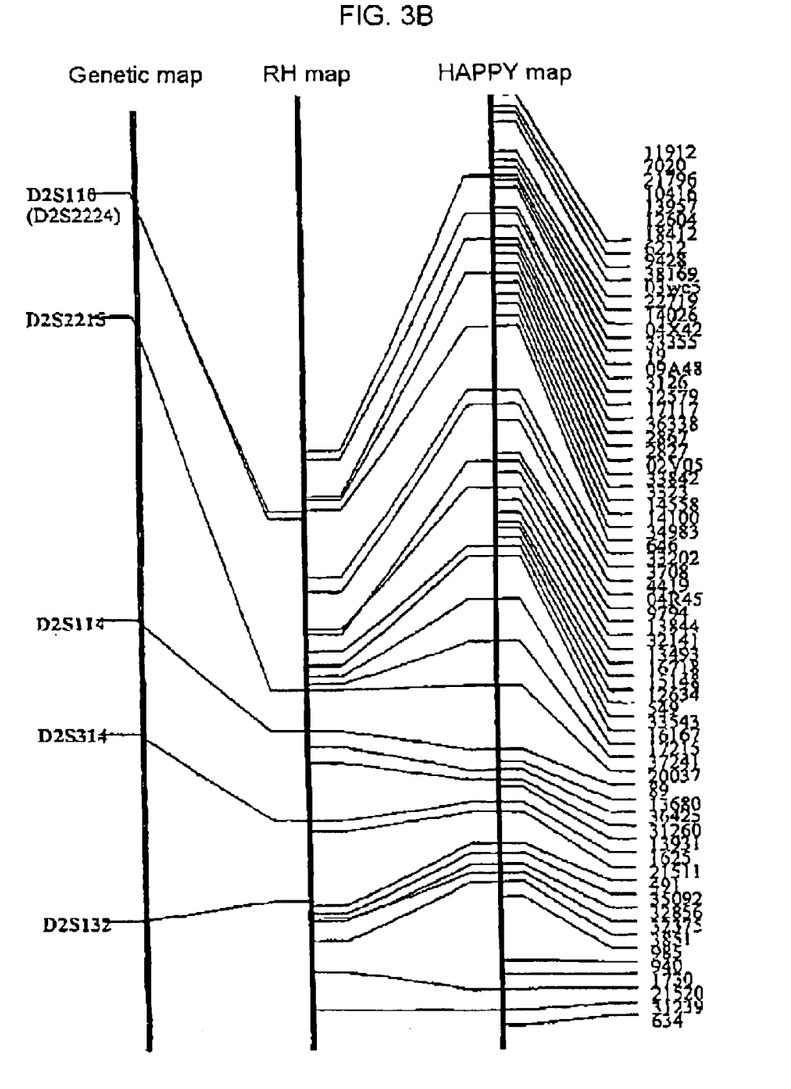

In order to validate the map mentioned above, the obtained data were compared with those available in the computer bases. Presently, a large number of data are available from the mapping by radiation hybrids or by family studies. The comparison of our results with those obtained with radiation hybrids on the G3 mapping panel which was obtained by irradiating cells at 10,000 rads (Stewart et al., 1997), was selected as a priority. The average size of the obtained fragments is about 4 Mb, which is very close to the size of fragments which we selected for forming our panel (5.5 Mb). 48 common markers were placed on both maps (FIG. 3). The general order of these markers is observed in both maps, as only 4 inversions were revealed. These two by two inversions are only observed on close markers on the genome at a distance estimated to be less than 500 kb to be compared with the panel's resolution limit rh (shgc.stanford.edu) estimated to be 300 kb. In the region immediately located above the centromere, three markers have a relatively divergent position. This may be correlated with the fact that mapping by radiation hybrids may cause biasses in the resolution of regions surrounding the centromere. This fact may also explain the differences in the distances separating the markers in these regions (FIG. 3). The position of the markers which we have obtained, is in good agreement with the genetic map available in the databases (FIG. 3).

REFERENCES

Apostolakos (1993) Anal. Biochem. 213, 277–284
Berndt (1995) Anal. Biochem. 225, 252–257
Boehnke M et al. (1991) Statistical methods for multipoint radiation hybrid Mapping. Am. J. Hum. Genet., 49, 1174–1188
Cheung V G and Nelson S F (1996) Whole genome amplification using a degenerate oligonucleotide primer allows hundreds of genotypes to be performed on less than one nanogram of genomic DNA. Proc. Natl. Acad. Sci. USA, 93, 14676–14679
Cox D R et al. (1990) Radiation hybrid Mapping: a somatic cell genetic method for constructing high-resolution maps of mammalian chromosomes. Science, 250, 245–250
Dear P H and Cook P (1993) Happy Mapping: linkage Mapping using a physical analogue of meiosis. Nucl. Acids Res., 21, 13–?0
Dear P H et al. (1998) A high resolution metric HAPPY map of human chromosome 14. Genomics 48, 232–241
Deloukas P et al. (1998) A Physical Map of 30,000 Human Genes. Science, 282, 744–746
Grothues D et al. (1993) PCR amplification of megabase DNA with tagged random primers (T-PCR). Nucleic Acids Res. 21, 1321–1322
Gyapay G et al. (1996) A radiation hybrid map of the human genome. Hum. Mol. Genet,5, 339–346
Kawai (1993) Anal. Biochem. 209, 63–69
Lander E S and Botstein D B (1989) Mapping mendelian factors underlying quantitative traits using RFLP linkage maps. Genetics. 121. 185–199
Piper M B et al., (1998) A HAPPY map of Crypto sporidium parvum. Genome research, 8, 1299–1307
Running (1990) Biotechniques, 8, 276–277
Slonim D et al. (1995) RHMAPPER: An interactive computer package for constructing radiation hybrid maps. Cold Spring Harbor Meeting on Genome Mapping and Sequencing. May 10–14
Stewart E A et al. (1997) An STS-based radiation hybrid map of the human genome. Genome Res., 7, 422–433
Telenius H et al. (1992) Degenerate Oligo-Primed PCR: General amplification of target DNA by a single degenerate primer. Genomics, 13, 718–725
Venter et al. (1998) Science compass June $5^{th}$, p. 1540.
Weber J L and Myers E W (1997) Human whole-genome shotgun sequencing. Genome Res., 7, 401–409
Zhang L et al. (1992) Whole genome amplification from a single cell: Implications for genetic analysis. Proc. Natl. Acad. Sci. USA, 89, 5847–5851

What is claimed is:

1. A method for mapping a DNA molecule comprising the steps:
   (A) breaking the DNA molecule in order to obtain DNA fragments, wherein the size of the fragments depends on a selected resolution,
   (B) distributing said fragments in receptacles in order to have an amount of DNA between about 0.5 to 1.5 DNA haploid genome equivalent per receptacle,
   (C) amplifying the DNA contained in the receptacles by an amplification method comprising the following steps: i) a first amplification by means of a primer comprising 10 to 30 defined nucleotides at its 5' end and 5 to 10 random nucleotides at its 3' end, ii) a second amplification by means of a primer comprising at least the defined oligonucleotides of the 5' end of the primer used in step i),
   (D) detecting the presence or absence of markers in the receptacles
   (E) calculating an order of the markers and a distance between the markers to obtain a map of the DNA molecule.

2. The method as claimed in claim 1, wherein the primer used in step i) comprises 20 defined nucleotides at its 5' end and 6 random nucleotides at its 3' end.

3. The method as claimed in claim 2, wherein the primer used in step i) has the sequence of SEQ ID NO. 1.

4. The method as claimed in claim 2, wherein the primer used in step ii) comprises the 20 defined nucleotides at the 5' end of the primer used in step i).

5. The method as claimed in claim 4, wherein the primer used in step ii) has the sequence of SEQ ID NO. 2.

6. The method as claimed in claim 1 wherein the DNA molecule is a genome, a chromosome, or a genome or chromosome fragment or is derived from a genome, a chromosome, or a genome or chromosome fragment.

7. The method as claimed in claim 6, wherein the DNA molecule is within a cell and the cell is encapsulated in agarose blocks and lysed to release the DNA molecule intact.

8. The method as claimed in claim 7, wherein the cells are plant or animal cells.

9. The method as claimed in claim 1 wherein the DNA molecule is broken by at least one of γ irradiation, enzymatic digestion, and mechanical action.

10. The method as claimed in claim 1 further comprising a step before the distribution step (B) wherein the DNA fragments are separated by pulsed field gel electrophoresis to obtain fragments of homogeneous sizes.

11. The method as claimed in claim 1, wherein the fragments are distributed in wells of a 96-, 182- or 384-well microtitration plate.

12. The method as claimed in claim 11, wherein the entire genetic information contained in the wells is amplified.

13. The method as claimed in claim 11, wherein the amplified DNA in each well is distributed to allow preparation of daughter plates.

14. The method as claimed in claim 13, wherein the markers are detected in wells of the daughter plates.

15. The method as claimed in claim 11, wherein the markers present in the wells are amplified by means of specific primers before the detection step.

16. The method as claimed in claim 10, wherein the detection is carried out directly after electrophoresis or with probes specific to the markers.

17. The method as claimed in claim 16, wherein the probes are capture probes, which are directly or indirectly immobilized on a solid support.

18. The method as claimed in claim 16 wherein the probes are marked by means of a marker including radioactive isotopes, enzymes capable of acting on a chromogenic, fluorigenic or luminescent substrate, and chromophore chemical compounds, chromogenic, fluorigenic and luminescent compounds.

19. The method as claimed in claim 1 wherein the detection is performed on DNA chips.

20. The method as claimed in claim 1 wherein the fragments are distributed in with 1 haploid genome equivalent per well in step (B).

* * * * *

SEQUENCE LISTING

<160> NUMBER OF SEQ ID NOS: 2

<210> SEQ ID NO 1
<211> LENGTH: 26

```
-continued

<212> TYPE: DNA
<213> ORGANISM: Artificial Sequence
<220> FEATURE:
<223> OTHER INFORMATION: Primer i
<223> OTHER INFORMATION: n means a, g, c ou t/u

<400> SEQUENCE: 1
aattaaccct cactaaaggg nnnnnn                                       26

<210> SEQ ID NO 2
<211> LENGTH: 20
<212> TYPE: DNA
<213> ORGANISM: Artificial Sequence
<220> FEATURE:
<223> OTHER INFORMATION: Primer ii

<400> SEQUENCE: 2
aattaaccct cactaaaggg                                              20
```